United States Patent

Cullen et al.

[11] Patent Number: 5,223,536
[45] Date of Patent: Jun. 29, 1993

[54] 1,4-DIARYL-1-CYCLOPROPYL-4-SUBSTITUTED BUTANES AS INSECTICIDES AND ACARICIDES

[75] Inventors: Thomas G. Cullen, Milltown, N.J.; Scott McN. Sieburth, Coram, N.Y.; Gary A. Meier, Robbinsville, N.J.; John F. Engel, Belmont, N.C.

[73] Assignee: FMC Corporation, Philadelphia, Pa.

[21] Appl. No.: 734,421

[22] Filed: Jul. 23, 1991

[51] Int. Cl.$^5$ .................. A01N 37/34; C07C 255/31
[52] U.S. Cl. ...................... 514/520; 514/521; 514/522; 514/523; 514/524; 514/525; 558/388; 558/404; 558/405; 558/407; 558/408; 558/409; 558/410; 568/639
[58] Field of Search ............. 558/410, 388, 404, 405, 558/407, 408, 409; 514/520, 719, 521, 523, 525, 522, 524

[56] References Cited

U.S. PATENT DOCUMENTS

| | | | |
|---|---|---|---|
| 4,261,920 | 4/1981 | Fuchs et al. | 558/410 |
| 4,287,208 | 9/1981 | Fuchs et al. | 558/410 X |
| 4,344,895 | 8/1982 | Martel et al. | 558/410 X |
| 4,594,196 | 6/1986 | Stoutamire et al. | 558/410 X |
| 4,791,098 | 12/1988 | Martin et al. | 558/388 X |
| 4,808,762 | 2/1989 | Meier et al. | 514/336 |
| 4,837,351 | 6/1989 | Torihara et al. | 558/388 |
| 4,940,780 | 7/1990 | Seitz et al. | 558/388 |

FOREIGN PATENT DOCUMENTS 2120664 7/1983 United Kingdom.

*Primary Examiner*—Joseph Paul Brust
*Attorney, Agent, or Firm*—Norman L. Craig; Robert M. Kennedy; Thomas G. Cullen

[57] ABSTRACT

The 1,4-diaryl-1-cyclopropyl-4-substituted butane pesticides of the following formula are effective as insecticides and acaricides:

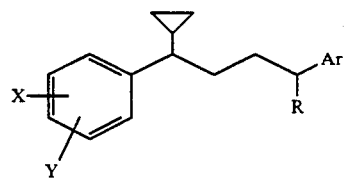

in which X and Y are independently hydrogen, halogen, alkyl, alkoxy, cycloalkylalkoxy, alkylcarbonyl, alkoxycarbonyl, haloalkyl, haloalkoxy, alkylthio, haloalkylthio, alkylsulfinyl, alkylsulfonyl, trialkylamino, nitro, or cyano; or X and Y together are —OCH$_2$O— or —OCF$_2$O— bridging the 2-3 or 3-4 positions of the phenyl ring;

Ar is 3-phenoxyphenyl, 4-fluoro-3-phenoxyphenyl, 6-phenoxypyridin-2-yl, or 2-methyl(1,1'-biphenyl)-3-yl;

R is cyano, methyl, trifluoromethyl, alkenyl, alkynyl, or halogen.

11 Claims, No Drawings

1,4-DIARYL-1-CYCLOPROPYL-4-SUBSTITUTED BUTANES AS INSECTICIDES AND ACARICIDES

This invention pertains to certain pyrethroid-like pesticides. More particularly, this invention concerns certain 1,4-diaryl-1-cyclopropyl-4-substituted butanes, pesticidal compositions thereof, and methods of using these compounds for pest control.

U.S. Pat. No. 4,808,762 discloses a class of pyrethroid-like compounds having the formula:

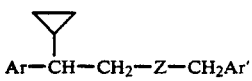

wherein

Ar is a substituted or unsubstituted phenyl, naphthyl or thienyl group;

Z is oxygen, sulfur, or methylene; and

Ar' is 2-methyl[1,1'-biphenyl]-3-yl, 3-phenoxyphenyl, 4-fluoro-3-phenoxyphenyl, or 6-phenoxy-2-pyridinyl with optional substitution of the phenyl, pyridinyl, or phenoxy moieties with halogen or lower alkyl.

These compounds are disclosed as having pyrethroid-like insecticidal and acaricidal activity and being relatively harmless to fish.

United Kingdom patent application GB 2 120 664A discloses a class of aromatic-substituted alkane derivatives having the following generic formula:

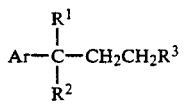

wherein

Ar is a substituted or unsubstituted phenyl or naphthyl group;

$R^1$ is a methyl, ethyl, or isopropyl group and $R^2$ is a hydrogen atom or a methyl group or $R^1 R^2$ taken together with the carbon to which they are attached represent a substituted or unsubstituted cycloalkyl group (specific examples of such groups include cyclopropyl, 2,2-dichlorocyclopropyl, cyclobutyl, cyclopentyl, and cyclohexyl); and $R^3$ stands for the residue of an alcohol, $R^3OH$, commonly found in natural or synthetic pyrethroids (specific examples include among others 3-phenoxyphenylethynylmethyl, 3-phenoxyphenylmethyl, 3-phenoxyphenylcyanomethyl, and 3-phenoxy-4-fluorophenylmethyl).

These compounds are asserted to have high insecticidal and acaricidal activity and to have low toxicity to mammals and fish.

The present invention pertains to a novel class of pesticidal 1,4-diaryl-1-cyclopropyl-4-substituted butanes. These compounds contain two asymmetric carbon atoms; the invention thus includes individual stereoisomers as well as racemic and non-racemic mixtures of enantiomers.

This invention also encompasses pesticidal compositions containing the compounds of this invention and their use for pest control. The compounds of this invention are effective for control of a wide variety of insects and acarids and are expected to be useful in situations in which pyrethroid pesticidal control is desired.

The 1,4-diaryl-1-cyclopropyl-4-substituted butanes of this invention may be represented by the following structural formula:

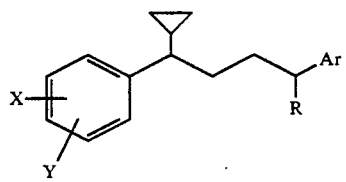

in which X and Y are independently hydrogen, halogen, alkyl, alkoxy, cycloalkylalkoxy, alkylcarbonyl, alkoxycarbonyl, haloalkyl, haloalkoxy, alkylthio, haloalkylthio, alkylsulfinyl, alkylsulfonyl, alkylamino, nitro, or cyano; or when taken together are —OCH$_2$O— or —OCF$_2$O— bridging the 2-3 or 3-4 positions on the phenyl ring. Ar is 3-phenoxyphenyl, 4-fluoro-3-phenoxyphenyl, 6-phenoxypyridin-2-yl, or 2-methyl-(1,1'-biphenyl)-3-yl. R is cyano, methyl, trifluoromethyl, alkynyl, alkenyl or halogen.

In this description unless contrary intent is clearly expressed, whenever the terms appear, "halo" or "halogen" means fluorine, chlorine, or bromine. The term "alkyl", "alkenyl", "haloalkyl", "alkoxy" or the like means a straight or branched hydrocarbon chain of 1-6 carbon atoms, preferably 1-4 carbon atoms. The term "cyclo" when used as a prefix to "alkyl", "haloalkyl" or the like means a saturated hydrocarbon ring of 3-6 carbon atoms. The term "halo" modifying "alkyl", "cycloalkyl", or "alkoxy" or the like means one or more hydrogen atoms has been replaced by halogen.

In a preferred embodiment X is chlorine, Y is hydrogen, R is cyano, and Ar is 3-phenoxyphenyl or 4-fluoro-3-phenoxyphenyl. Other preferred compounds include those in which X is chlorine, fluorine, trifluoromethyl, or trifluoromethoxy, Y is fluorine or hydrogen, R is cyano, and Ar is 3-phenoxyphenyl or 4-fluoro-3-phenoxyphenyl.

Using commercially available starting materials the compounds of this invention may be prepared using procedures described in the following examples, or by modifications to synthesis techniques which are known in the art.

The 1,4-diaryl-1-cyclopropyl-4-cyanobutanes of this invention may be prepared by reacting the appropriately 4-substituted benzoyl chloride with N-methoxy-N-methylamine hydrochloride in triethylamine and methylene chloride to yield the corresponding benzamide. The benzamide or an appropriately substituted benzonitrile is then reacted with cyclopropyl magnesium bromide to give the corresponding substituted phenyl cyclopropyl ketone, which in turn is reacted with trimethyl or triethyl phosphonoacetate and sodium hydride in dimethylformamide, or ethyl (trimethylsilyl) acetate and lithium diisopropylamide in tetrahydrofuran at −78° C. to give an alkyl 3-cyclopropyl-3-phenylpropenoate. This compound is then reduced with magnesium metal in methanol to give the propanoate, which may then be further reduced with lithium aluminum hydride to give the 3-cyclopropyl-3-phenylpropan-1-ol. This alcohol is oxidized with pyridium chlorochromate in methylene chloride to give the corresponding aldehyde, which is in turn reacted with the appropriate phenoxyphenyl acetonitrile and sodium methoxide in methanol. The resulting 1,4-diaryl-4-cyano-3-butene is then reduced with magnesium metal in methanol to give the required 1,4-diaryl-1-cyclopropyl-4-cyclobutane. Examples 1-3 describe in detail the synthesis outlined above.

Those compounds in which the 4-butyl substituent R is alkyl (for example methyl) may be prepared using a cyclopropyl appropriately substituted phenyl ketone, (for example, cyclopropyl 4-chlorophenyl ketone). These ketones are commercially available or may be prepared using procedures such as those described in Example 2, Step E, or Example 3, Step A. The cyclopropyl ketone is reacted with vinylmagnesium bromide in tetrahydrofuran, yielding the corresponding 1-cyclopropyl-1-(appropriately substituted phenyl)-2-propen-1-ol. This alcohol is then reacted with thionyl chloride and pyridine in diethyl ether to give the corresponding 1-cyclopropyl-1-(appropriately substituted phenyl)-3-chloro-1-propene. The chloropropene is in turn reacted with triphenylphosphine in toluene to give the corresponding 3-cyclopropyl-3-(appropriately substituted phenyl)-2-propenyltriphenylphosphonium chloride, (for example, 3-cyclopropyl-3-(4-chlorophenyl)-2-propenyltriphenylphosphonium chloride).

A second intermediate, an alkyl aryl ketone, (for example, methyl (4-fluoro-3-phenoxyphenyl) ketone) may be prepared by the reaction of the appropriate aryl aldehyde, (for example, 4-fluoro-3-phenoxybenzaldehyde), with an alkyl Grignard reagent, (for example, a methylmagnesium bromide) in diethyl ether, affording the corresponding 1-aryl alkyl alcohol, (for example, 1-(4-fluoro-3-phenoxyphenyl)ethanol). This alcohol is in turn oxidized with pyridinium chlorochromate in methylene chloride to give the corresponding alkyl aryl ketone, (for example, methyl (4-fluoro-3-phenoxyphenyl) ketone).

The alkyl aryl ketone is then reacted with the 3-cyclopropyl-3-(appropriately substituted phenyl)-2-propenyltriphenylphosphonium chloride described above and n-butyllithium in tetrahydrofuran to give the corresponding 1-cyclopropyl-1-(appropriately substituted aryl)-4-alkyl-4-aryl-1,3-diene, (for example, 1-cyclopropyl-1-(4-chlorophenyl)-4-(4-fluoro-3-phenoxyphenyl)-1,3-pentadiene). The 1,3-diene is then reduced with magnesium metal in methanol, yielding the corresponding 1-cyclopropyl-1-(appropriately substituted phenyl)-4-alkyl-4-aryl-2-alkene (for example, 1-cyclopropyl-1-(4-chlorophenyl)-4-(4-fluoro-3phenoxyphenyl)-2-pentene). Hydrogenation of the 2-alkene in the presence of 10% palladium on charcoal in ethanol gives the desired 1-cyclopropyl-1(appropriately substituted phenyl)-4-alkyl-4-arylalkane (for example, 1-cyclopropyl-1-(4-chlorophenyl)-4-(4-fluoro-3-phenoxyphenyl)pentane.

The compounds of the present invention in which R is trifluoromethyl may be prepared in a manner similar to that described above. An aryl trifluoromethyl ketone is reacted with the previously described 3-cyclopropyl-3-(appropriately substituted aryl)-2-propenyltriphenylphosphonium chloride and n-butyllithium in tetrahydrofuran, affording the corresponding 1-cyclopropyl-1-(appropriately substituted phenyl)-4-trifluoromethyl-4-aryl-1,3-diene. Treatment of the 1,3-diene as described above (see Example 4, Steps G-H) affords the corresponding 1-cyclopropyl-1-(appropriately substituted phenyl)-4-trifluoromethyl-4-arylalkane (for example, 1-cyclopropyl-1-(4-chlorophenyl)-4-(4-fluoro -3-phenoxyphenyl)-5,5,5-trifluoropentane).

Various methods known to those with ordinary skill in the art may be used to prepare the aryl trifluoromethyl ketone intermediates.

An intermediate common to many of these methods is N-methoxy-N-methyl-2,2,2-trifluoroacetamide. This intermediate may be prepared by the reaction of trifluoroacetyl chloride and N-methoxy-N-methylamine hydrochloride under basic conditions in a manner similar to that shown in Example 2.

The Grignard reagents of 2-bromo-6-phenoxypyridine, 3-phenoxyphenyl bromide, and 3-chloro-2-methylbiphenyl may be prepared using standard techniques. These compounds may be reacted with the previously described N-methoxy-N-methyl-2,2,2-trifluoroacetamide in tetrahydrofuran using a procedure similar to that shown in Example 2, Step E. This reaction affords the corresponding aryl trifluoromethyl ketone. The preparation of the intermediates, 2-bromo-6-phenoxypyridine and 3-chloro-2-methylbiphenyl, from which the Grignard reagents are prepared as herein described. The intermediate 3-phenoxyphenyl bromide may be prepared by the reaction of the sodium salt of phenol and 1,3-dibromobenzene in the presence of cuprous bromide in diglyme.

Trifluoromethyl 4-fluoro-3-phenoxyphenyl ketone may be prepared using the following procedure. Bromination of 2-fluoroanisole yields a mixture of bromo-2-fluoroanisole isomers from which 5-bromo-2-fluoroanisole is isolated. The Grignard reagent of 5-bromo-2-fluoroanisole is then prepared and is in turn reacted with N-methoxy-N-methyl-2,2,2-trifluoroacetamide in tetrahydrofuran, yielding trifluoromethyl 4-fluoro-3-methoxyphenyl ketone. This ketone is protected by formation of the corresponding ketal, which is in turn treated with trimethylsilyl iodide, sodium hydroxide, bromobenzene, and acid, yielding trifluoromethyl (4-fluoro-3-phenoxyphenyl) ketone.

The compounds of the present invention in which R is alkenyl or alkynyl (for example, ethenyl or ethynyl) may be prepared by brominating an aryl alkyl ketone (for example, methyl (4-fluoro-3-phenoxyphenyl) ketone), under basic conditions, to give the corresponding aryl bromoalkyl ketone. This intermediate is treated with sodium hydride and then with phenylmethanol to give an aryl (phenylmethoxymethyl) ketone. This ketone is in turn reacted with 3-cyclopropyl-3-(appropriately substituted phenyl)-2-propenyltriphenylphosphonium chloride and n-butyllithium in tetrahydrofuran, affording the corresponding 1-cyclopropyl-1-(appropriately substituted phenyl)-4-aryl-4-(phenylmethoxymethyl)-1,3-butadiene. Hydrogenation of the 1,3-diene in turn yields 5-cyclopropyl-5-(appropriately substituted phenyl)-2-arylpentan-1-ol. Oxidation of this alcohol affords the corresponding 5-cyclopropyl-5-(appropriately substituted phenyl)-2-arylpentanal, which in turn is treated with methyltriphenylphosphonium bromide and then with n-butyllithium in tetrahydrofuran to give the desired 1-cyclopropyl-1-(appropriately substituted phenyl)-4-aryl-5-hexene (for example, 1-cyclopropyl-1-(4-chlorophenyl)-4-(4-fluoro -3-phenoxyphenyl)-5hexene). Treatment of the hexene with bromine under basic conditions will afford the desired hexyne derivative (for example, 1-cyclopropyl-1-(4-chlorophenyl)-4-(4-fluoro-3-phenoxyphenyl)-5-hexyne.

The compounds of the present invention in which R is halogen (for example, bromine) may be prepared by one of ordinary skill in the art. A 1-cyclopropyl-1-(appropriately substituted aryl)-2-propen-1-ol, previously described (for example, 1-cyclopropyl-1-(4-chlorophenyl)-2-propen-1-ol) is treated with pyridinium chlorochromate in methylene chloride, to give the corresponding 3-cyclopropyl-3-(appropriately substituted aryl)-2-propenal.

A second intermediate, an arylmethyltriphenylphosphonium chloride (for example, 4-fluoro-3-phenoxyphenylmethyltriphenylphosphonium chloride) is prepared by the reaction of the corresponding arylmethyl chloride with triphenylphosphine in tetrahydrofuran. The arylmethyltriphenylphosphonium chloride is treated with n-butyllithium in tetrahydrofuran at −78° C. and is then reacted with the 3-cyclopropyl-3-(appropriately substituted)-2-propenal described above, to give the corresponding 1-cyclopropyl-1-(appropriately substituted phenyl)-4-aryl-1,3-butadiene. The butadiene is then hydrogenated in the presence of Raney nickel in ethanol, affording the 1-cyclopropyl-1- appropriately substituted phenyl)-4-arylbutane. The aryl butane is halogenated with, for example, N-halosuccinimide in carbon tetrachloride in the presence of light to yield the desired 1-cyclopropyl-1-(appropriately substituted phenyl)-4halobutane, (for example, 1-cyclopropyl-1-(4-fluoro-3-phenoxyphenyl)-4-bromobutane).

Many of the appropriately substituted benzoic acid chloride intermediates disclosed herein are available commercially or may be readily prepared from the corresponding acids. Others may be prepared using methods known to one of ordinary skill in the art. Methyl 2,3-dihydroxybenzoate, for example, may be reacted under basic conditions with dibromomethane, to give methyl 2,3-methylenedioxybenzoate. This methylenedioxy bridged intermediate is in turn subjected to alkaline hydrolysis with sodium hydroxide in water, yielding the corresponding 2,3-methylenedioxybenzoic acid, which is then converted to the corresponding benzoic acid chloride.

Methyl 2,3-methylenedioxybenzoate disclosed above, may be alternatively reacted with phosphorus pentachloride to give methyl 2,3-dichloromethylenedioxybenzoate. The chlorinated intermediate is subsequently reacted with antimony trifluoride in dioxane, yielding methyl 2,3-difluoromethylenedioxybenzoate. This methyl ester is hydrolyzed to the acid, which is then converted to the corresponding acid chloride.

In a similar synthesis method, 1,2-methylenedioxybenzene may be converted to 1,2-difluoromethylenedioxybenzene using phosphorus pentachloride, followed by the reaction with antimony trifluoride in dioxane. The 1,2-difluoromethylenedioxybenzene is then brominated in the presence of iron filings in carbon tetrachloride, to afford 3,4-difluoromethylenedioxy bromobenzene. The bromobenzene is treated with n-butyllithium in tetraghydrofuran at −78° C. and then with carbon dioxide to give 3,4-difluoromethylenedioxybenzoic acid. The acid is in turn converted to the corresponding acid chloride by methods previously described.

The aryl-substituted acetonitrile intermediates disclosed herein may also be prepared by methods known by one of ordinary skill in the art. Generally, the aryl-substituted acetonitrile intermediates may be prepared by reacting an appropriate aryl substituted methanol with thionyl chloride and a catalytic amount of pyridine in toluene to give the corresponding arylsubstituted methyl chloride (Example 2, Step B), which is in turn reacted with potassium cyanide and 1,4,7,10,13,16-hexaoxacyclooctadecane in tetrahydrofuran to give the corresponding aryl-substituted acetonitrile (Example 2, Step C).

The aryl-substituted methanol intermediates used to prepare the aryl-substituted acetonitrile may be prepared in different ways, also known by one of ordinary skill in the art. For example, (2-methyl[1,1'-biphenyl]-3-yl)methanol may be prepared from 2,6-dichlorotoluene and bromobenzene as described in U.S. Pat. No. 4,507,513 and U.S. Pat. No. 4,740,637.

The 3-phenoxyphenylmethanol and 4-fluoro-3-phenoxyphenylmethanol intermediates may be prepared by the reaction of the corresponding commercially available phenoxybenzaldehyde with lithium aluminum hydride and water under basic conditions (Example 2, Step A).

The 6-phenoxy-2-pyridinylmethanol may be prepared by first reacting phenol with 2,6-dibromopyridine in dimethyl sulfoxide under basic conditions to give 2-bromo-6-phenoxypyridine. This compound is then reacted at −70° C. with n-butyllithium in diethyl ether and then with dimethylformamide at −30° C. to give 2-formyl-6-phenoxypyridine. This aldehyde is in turn reacted with sodium borohydride in methanol, yielding the corresponding 6-phenoxy-2-pyridinylmethanol.

The examples which follow illustrate specific methods for preparing the compounds of this invention.

EXAMPLE 1

Synthesis of
1-cyclopropyl-1-(4-chlorophenyl)-4-cyano-4-(3-phenoxyphenyl)butane

Step A Methyl 3-cyclopropyl-3-(4-chlorophenyl)-propenoate

A 50% suspension of 5.7 grams (0.012 mole) of sodium hydride in mineral oil was washed with three portions of tetrahydrofuran, and to this was added 21.7 grams (0.012 mole) of trimethyl phosphonoacetate in 300 mL of tetrahydrofuran. To the resultant thick mixture was added 150 ml of dimethylformamide. This was followed by the addition of a solution of 19.6 grams (0.011 mole) of cyclopropyl 4-chlorophenyl ketone in 50 ml of dimethylformamide. Upon completion of addition, the reaction mixture was heated to 80° C. and it was stirred for five hours. Gas chromatography of the reaction mixture indicated the presence of unreacted ketone. The reaction mixture was cooled, and an additional 1.0 gram of 97% sodium hydride was added. Upon completion of addition, the reaction mixture was again warmed to 80° C. and stirred for about 18 hours. Gas chromatography analysis of the reaction mixture indicated that unreacted ketone was still present. An additional 0.8 gram of 97% sodium hydride and 4.0 grams of trimethyl phosphonoacetate were added, and the reaction mixture was heated at 80° C. for an additional six hours. After this time the reaction mixture was cooled and poured into 500 ml of water and 300 ml of diethyl ether. The diethyl ether layer was separated, and the aqueous layer was extracted with five portions of diethyl ether. The ether layer and the extracts were combined and were washed with four portions of water. The aqueous layer and the water washes were combined and extracted with two portions of diethyl ether. The two ether extracts were combined and were washed with four portions of water. All of the organic layers and diethyl ether washes were combined and dried with magnesium sulfate. The mixture was filtered, and the filtrate was concentrated under reduced pressure, yielding 24.0 grams of methyl 3-cyclopropyl-3-(4-chlorophenyl)propenoate.

Step B Methyl 3-cyclopropyl-3-(4-chlorophenyl)propanoate

A mixture of 17.0 grams (0.072 mole) of methyl 3-cyclopropyl-3-(4-chlorophenyl)propenoate and 4.3 grams (0.18 mole) of magnesium in 250 ml of methanol was stirred at ambient temperature for about 3.5 hours. After this time the reaction mixture was carefully diluted with aqueous 3N hydrochloric acid. The mixture was extracted with diethyl ether. The combined ether extracts were dried with sodium sulfate and filtered. The filtrate was concentrated under reduced pressure to a residual oil. The oil was distilled under vacuum, yielding 10.7 grams of methyl 3-cyclopropyl-3-(4-chlorophenyl)propanoate; b.p. 91–97° C./0.10 mm. The spectrum was consistent with the proposed structure.

Step C 3-Cyclopropyl-3-(4-chlorophenyl)propan-1-ol

A stirred solution of 10.7 grams (0.045 mole) of methyl 3-cyclopropyl-3-(4-chlorophenyl)propanoate in 45 ml of tetrahydrofuran was cooled to 0° C., and 45 ml of 1.0 M of lithium aluminum hydride in tetrahydrofuran was added slowly during a one hour period. Upon completion of addition, the reaction mixture was stirred at 0° C. for two hours and then was allowed to warm to ambient temperature. The reaction was quenched by the sequential addition of 2 ml of water, 2 ml of aqueous 15% sodium hydroxide, and 6 ml of water. The reaction mixture was taken up in 100 ml of diethyl ether. The solution was filtered, and the filtrate was dried with sodium sulfate. The mixture was filtered, and the filtrate was concentrated under reduced pressure, yielding 9.3 grams of 3-cyclopropyl-3-(4-chlorophenyl)propan-1-ol.

Step D 3-Cyclopropyl-3-(4-chlorophenyl)propionaldehyde

A mixture of 6.5 grams (0.03 mole) of pyridinium chlorochromate in 25 ml of methylene chloride was stirred, and a solution of 2.1 grams (0.03 mole) of 3-cyclopropyl-3-(4-chlorophenyl)propan-1-ol in 5 ml of methylene chloride was quickly added. Upon completion of addition, the reaction mixture was stirred at ambient temperature for one hour. The reaction mixture was then diluted with 100 ml of diethyl ether, and this mixture was filtered through a pad of activated magnesium silicate. The filtrate was concentrated under reduced pressure, yielding 1.5 grams of 3-cyclopropyl-3-(4-chlorophenyl)propionaldehyde.

Step E 1-Cyclopropyl-1-(4-chlorophenyl)-4-cyano-4-(3-phenoxyphenyl)-3-butene A mixture of 1.5 grams (0.007 mole) of 3-cyclopropyl-3-(4-chlorophenyl)propionaldehyde and 1.5 grams (0.007 mole) of 3-phenoxyphenylacetonitrile in 50 ml of methanol was stirred, and 0.7 ml of 25% sodium methoxide in methanol was added quickly. Upon completion of addition, the reaction mixture was stirred at ambient temperature for four hours. The reaction mixture was then concentrated, and the residue was taken up in 100 ml of diethyl ether. The ether solution was washed with two 100 ml portions of water. The ether layer was dried with sodium sulfate and filtered. The filtrate was concentrated under reduced pressure to a residue. The residue was subjected to centrifugally accelerated, radial thin layer chromatography. Elution was accomplished using 5% diethyl ether in hexane. The appropriate fractions were combined and concentrated under reduced pressure, yielding 1.9 grams of 1-cyclopropyl-1-(4-chlorophenyl)-4-cyano-4-(3-phenoxyphenyl)-3-butene. The nmr spectrum was consistent with the proposed structure.

Step F 1-Cyclopropyl-1 (4-chlorophenyl)-4-cyano-4-(3-phenoxyphenyl)butane

A solution of 0.9 gram (0.002 mole) of 1-cyclopropyl-1-(4-chlorophenyl) -4-cyano-4-(3-phenoxyphenyl)-3-butene in 15 ml of methanol was stirred, and 0.5 gram (0.002 mole) of magnesium was added. The reaction mixture was stirred for about one hour at which time an exothermic reaction occurred. The reaction mixture was cooled to 0° C. where it was stirred for one hour, and then it was allowed to warm to ambient temperature where it stirred for two hours. After this time the reaction mixture was diluted with 20 ml of aqueous 10% hydrochloric acid, and the mixture was extracted with diethyl ether. The combined extracts were dried with magnesium sulfate and filtered. The filtrate was concentrated under reduced pressure, yielding 0.7 gram of 1-cyclopropyl-1-(4-chlorophenyl)-4-cyano-4-(3-phenoxyphenyl)butane. The nmr spectrum was consistent with the proposed structure.

EXAMPLE 2

Synthesis of 1-cyclopropyl-1-(4-trifluoromethylphenyl)-4-cyano -4-(4-fluoro-3-phenoxyphenyl)butane

Step A 4-Fluoro-3-phenoxyphenylmethanol

A suspension of 1.4 grams (0.038 mole) of lithium aluminum hydride in 50 ml of anhydrous diethyl ether was stirred, and a solution of 21.6 grams (0.1 mole) of commercially available 4-fluoro-3-phenoxybenzaldehyde in 50 ml of anhydrous diethyl ether was added dropwise during a one hour period. Upon completion of addition, the reaction mixture was heated at reflux for 1.0 hour. The reaction mixture was cooled to 15° C., and 1.4 ml of water was cautiously added dropwise. Upon completion of addition, the reaction mixture was again cooled to 15° C., and 1.4 ml of an aqueous, 15% sodium hydroxide solution was added dropwise. This was followed by the addition of 4.2 ml of water. The mixture was filtered through diatomaceous earth, and the filtrate was concentrated under reduced pressure, yielding 19.5 grams of 4-fluoro-3-phenoxyphenylmethanol as an oil.

Step B 4-Fluoro-3-phenoxyphenylmethyl chloride

A solution of 12.6 grams (0.106 mole) of thionyl chloride and a catalytic amount of pyridine in 25 ml of toluene was stirred, and a solution of 19.5 grams (0.88 mole) of 4-fluoro-3-phenoxyphenylmethanol in 30 ml of toluene was added dropwise during a 45 minute period. The reaction mixture temperature was maintained at 25–35° C. throughout the addition. Upon completion of addition, the reaction mixture was warmed to 45° C. after which stirring was continued for one hour. The reaction mixture was cooled and then was concentrated under reduced pressure, yielding 23.5 grams of semisolid product. This material was combined with 114.2 grams of identical material which had been obtained from a large run of the present reaction. The 136.6 grams of material was distilled under reduced pressure, and the appropriate fractions were combined, yielding 100.3 grams of 4-fluoro-3-phenoxyphenylmethyl chloride, b.p. 98–105° C./0.03–0.13 mm Hg.

Step C 4-Fluoro-3-phenoxyphenylacetonitrile

A stirred mixture of 5.0 grams (0.021 mole) of 4-fluoro-3-phenoxyphenylmethyl chloride, 4.1 grams (0.063 mole) of potassium cyanide and 0.6 gram (0.002 mole) of 1,4,7,10,13,16-hexaoxacyclooctadecane in 180 ml of tetrahydrofuran was heated at reflux for about four hours. After this time the reaction mixture was diluted with 180 ml of water, and then extracted with two 100 ml portions of diethyl ether. The combined ether extracts were washed with five 200 ml portions of water. The organic layer was dried with magnesium sulfate and filtered. The filtrate was concentrated under reduced pressure, yielding 5.4 grams of 4-fluoro-3-phenoxyphenylacetonitrile. The nmr spectrum was consistent with the proposed structure.

Step D
N-methoxy-N-methyl-4-trifluoromethylbenzamide

A suspension of 19.9 grams (0.204 mole) of N-methoxy-N-methylamine hydrochloride in 500 ml of methylene chloride was stirred, and 39.3 grams (0.389 mole) of triethylamine was added. Upon completion of addition, the reaction mixture was stirred for ten minutes, and a solution of 4-trifluoromethylbenzoyl chloride in 25 ml of methylene chloride was added dropwise. Upon completion of addition, the reaction mixture was stirred at ambient temperature for 18 hours. After this time the reaction mixture was stirred vigorously with 300 ml of water. The aqueous layer was separated from the organic layer and was washed with three portions of methylene chloride. The washes were combined with the organic layer, and the combination was dried with magnesium sulfate. The mixture was filtered, and the filtrate was concentrated under reduced pressure, yielding 42.5 grams of N-methoxy-N-methyl-4-trifluoromethylbenzamide as an oil. The nmr spectrum was consistent with the proposed structure.

Step E Cyclopropyl (4-trifluoromethylphenyl) ketone

Under a nitrogen atmosphere a vigorously stirred solution of 42.5 grams (0.182 mole) of N-methoxy-N-methyl-4-trifluoromethylbenzamide in 250 ml of dry tetrahydrofuran was cooled to 0–10° C., and 41.7 grams (0.287 mole) of freshly prepared cyclopropylmagnesium bromide in 170 ml of tetrahydrofuran was added rapidly dropwise. Upon completion of addition, the reaction mixture was allowed to warm to ambient temperature where it was stirred for about 60 hours. At the end of this time the reaction mixture was concentrated under reduced pressure to a residue. The residue was taken up in water and extracted with four portions of methylene chloride. The combined extracts were dried with magnesium sulfate and filtered. The filtrate was passed through a pad of silica gel and was concentrated under reduced pressure yielding, 34.6 grams of cyclopropyl (4-trifluoromethylphenyl) ketone. The nmr spectrum was consistent with the proposed structure.

Step F Ethyl
3-cyclopropyl-3-(4-trifluoromethylphenyl)propenoate

A stirred solution of 4.1 grams (0.04 mole) of diisopropylamine in 100 ml of tetrahydrofuran was cooled to −78° C., and 17.4 ml (0.04 mole) of 2.3 M n-butyllithium in hexane was added during a 15 minute period. Upon completion of addition, the reaction mixture was stirred at −78° C. for 15 minutes. After this time, 6.4 grams (0.04 mole) of ethyl (trimethylsilyl)acetate was added during a 10 minute period. Upon completion of addition, the reaction mixture was stirred at −78° C. for 30 minutes, and 8.5 grams (0.04 mole) of cyclopropyl (4-trifluoromethylphenyl) ketone was added during a 5 minute period. After this time the reaction mixture was stirred at −78° C. for one hour, at −25° C. for one hour, and finally at ambient temperature for two hours. The reaction was then quenched with aqueous 5% hydrochloric acid. The mixture was then extracted with diethyl ether, and the combined extracts were dried with sodium sulfate. The mixture was filtered, and the filtrate was concentrated under reduced pressure to a residue. The residue was subjected to column chromatography on silica gel. Elution was accomplished using 5% diethyl ether in hexane. The appropriate fractions were combined and concentrated under reduced pressure, yielding 6.0 grams of ethyl 3-cyclopropyl-3-(4-trifluoromethylphenyl)propenoate. The nmr spectrum was consistent with the proposed structure.

Step G Methyl
3-cyclopropyl-3-(4-trifluoromethylphenyl)propanoate

This compound was prepared in a manner analogous to that of Example 1, Step B, using 3.2 grams 0.011 mole) of ethyl 3-cyclopropyl-3-(4-trifluoromethylphenyl)-propenoate and 2.7 grams (0.011 mole) of magnesium in 25 ml of methanol. The yield of methyl 3-cyclopropyl-3-(4-trifluoromethylphenyl)propanoate was 2.7 grams.

Step H
Cyclopropyl-1-(4-trifluoromethylphenyl)propan-3-ol

This compound was prepared in a manner analogous to that of Example 1, Step C, using 2.7 grams (0.01 mole) of methyl 3-cyclopropyl-3-(4-trifluoromethylphenyl)propanoate, 7.5 ml (0.075 mole) of 1.0 M lithium aluminum hydride in tetrahydrofuran, and 25 ml of tetrahydrofuran. The yield of 3-cyclopropyl-3-(4-trifluoromethylphenyl)-propan-1-ol was 2.5 grams. The nmr spectrum was consistent with the proposed structure.

Step I
3-Cyclopropyl-3-(4-trifluoromethylphenyl)-propionaldehyde

This compound was prepared in a manner analogous to that of Example 1, Step D, using 2.5 grams (0.01 mole) of 3-cyclopropyl-3-(4-trifluoromethylphenyl)-propan-1-ol and 8.6 grams (0.04 mole) of pyridinium chlorochromate in 50 ml of methylene chloride. The yield of 3-cyclopropyl-3-pressure (4-trifluoromethylphenyl)propionaldehyde was 1.4 grams.

Step J
1-Cyclopropyl-1-(4-trifluoromethylphenyl)-4-cyano-4-(4-fluoro -3-phenoxyphenyl)-3-butene This compound was prepared in a manner analogous to that of Example 1, Step E, using 0.73 gram (0.003 mole) of 3-cyclopropyl-3-(4-trifluoromethylphenyl)-propionaldehyde, 0.68 gram (0.003 mole) of 4-fluoro-3-phenoxyphenylacetonitrile (as prepared in Steps A–C), and 2.0 ml of methanolic 25% sodium methylate in 30 ml of methanol. The yield of 1-cyclopropyl-1-(4-trifluoromethylphenyl) -4-cyano-4-(4-fluoro-3-phenoxyphenyl)-3-butene was 1.51 grams. The nmr spectrum was consistent with the proposed structure.

Step K
1-cyclopropyl-1-(4-trifluoromethylphenyl)-4-cyano-4-(4-fluoro-3-phenoxyphenyl)butane This compound was prepared in a manner analogous to that of Example 1, Step F, using 0.70 gram (0.0016 mole) of 1-cyclopropyl-1-(4-trifluoromethylphenyl)-4-cyano-4-(4-fluoro-3-phenoxyphenyl)-3-butene and 0.38 gram (0.016 mole) of magnesium in 15 ml of methanol. The yield of 1-cyclopropyl -1-(4-trifluoromethylphenyl)-4-cyano-4-(4-fluoro-3-phenoxyphenyl)butane was 0.48 gram. The nmr spectrum was consistent with the proposed structure.

EXAMPLE 3

Synthesis of
1-cyclopropyl-1-(4-trifluoromethoxyphenyl)-4-cyano-4-(4-fluoro-3-phenoxyphenyl)butane

Step A Cyclopropyl 4-trifluoromethoxyphenyl ketone

Cyclopropylmagnesium bromide was prepared by adding 3.3 grams (0.11 mole) of cyclopropyl bromide to 2.9 grams (0.12 mole) of magnesium in refluxing tetrahydrofuran. Upon completion of addition, the Grignard reagent was stirred at reflux for one hour and then was cooled to ambient temperature. To this was added dropwise a solution of 20.5 grams (0.11 mole) of 4-trifluoromethoxybenzonitrile in tetrahydrofuran. Upon completion of addition, the reaction mixture was warmed to a temperature just below reflux at which temperature it was stirred for about 18 hours. The reaction mixture was cooled to ambient temperature, and 40 ml of methanol was added dropwise. Upon completion of addition, the reaction mixture was stirred for two hours and then was filtered. The filtrate was stirred for about 60 hours with about 25 grams of silica gel and 100 ml of water. The mixture was filtered, and the filtrate was diluted with ethyl acetate. The mixture was washed with water, and the organic layer was dried with magnesium sulfate. The mixture was then filtered, and the filtrate was concentrated under reduced pressure, yielding 12.4 grams of cyclopropyl 4-trifluoromethoxyphenyl ketone.

Step B Ethyl 3-cyclopropyl-3-(4-trifluoromethoxyphenyl)propenoate

This compound was prepared in a manner analogous to that of Example 1, Step A, using 10.0 grams (0.043 mole) of cyclopropyl 4-trifluoromethoxyphenyl ketone, 10.7 grams (0.048 mole) of triethyl phosphonoacetate and 1.3 grams (0.052 mole) of 97% sodium hydride in dimethylformamide. The yield of ethyl 3-cyclopropyl-3-(4-trifluoromethoxyphenyl)propenoate was 12.5 grams. The nmr spectrum was consistent with the proposed structure.

Step C Methyl 3-cyclopropyl-3-(4-trifluoromethoxyphenyl)propanoate

This compound was prepared in a manner analogous to that of Example 1, Step B, using 12.1 grams (0.040 mole) of ethyl 3-cyclopropyl-3-(4-trifluoromethoxyphenyl)-propenoate and 9.7 grams (0.40 mole) of magnesium in 100 ml of methanol. The yield of methyl 3-cyclopropyl-3-(4-trifluoromethoxyphenyl)propanoate was 10.1 grams. The nmr spectrum was consistent with the proposed structure.

Step D 3-Cyclopropyl-3-(4-trifluoromethoxyphenyl)-propan-1-ol

This compound was prepared in a manner analogous to that of Example 1, Step C, using 9.6 grams (0.033 mole) of methyl 3-cyclopropyl-3-(4-trifluoromethoxyphenyl)-propanoate and 1.4 grams (0.037 mole) of lithium aluminum hydride in 100 ml of tetrahydrofuran. The yield of 3-cyclopropyl-3-(4-trifluoromethoxyphenyl)propan-1-ol was 7.2 grams. The nmr spectrum was consistent with the proposed structure.

Step E 3-Cyclopropyl-3-(4-trifluoromethoxyphenyl)-propionaldehyde

This compound was prepared in a manner analogous to that of Example 1, Step D, using 7.2 grams (0.028 mole) of 3-cyclopropyl-3-(4-trifluoromethoxyphenyl)-propan-1-ol and 13.5 grams (0.063 mole) of pyridinium chlorochromate in methylene chloride. The yield of 3-cyclopropyl-3-(4-trifluoromethoxyphenyl)propionaldehyde was 3.7 grams. The nmr spectrum was consistent with the proposed structure.

Step F 1-Cyclopropyl-1-(4-trifluoromethoxyphenyl)-4-cyano-4-(4-fluoro-3-phenoxyphenyl)-3-butene This compound was prepared in a manner analogous to that of Example 1, Step E, using 1.7 grams 0.065 mole) of 3-cyclopropyl-3-(4-trifluoromethoxyphenyl)-propionaldehyde, 1.5 grams (0.065 mole) of 4-fluoro-3-phenoxyacetonitrile, and 1 ml of methanolic 25% sodium methoxide in methanol. The yield of 1-cyclopropyl-1-(4-trifluoromethoxyphenyl) -4-cyano-4-(4-fluoro-3-phenoxyphenyl)-3-butene was 1.1 grams. The nmr spectrum was consistent with the proposed structure.

Step G 1-Cyclopropyl-1-(4-trifluoromethoxyphenyl)-4-cyano-4-(4-fluoro-3-phenoxyphenyl)butane This compound was prepared in a manner analogous to that of Example 1, Step F, using 0.87 gram (0.0019 mole) of 1-cyclopropyl-1-(4-trifluoromethoxyphenyl)-4-cyano-4-(4-fluoro-3-phenoxyphenyl)-3-butene and 0.46 gram (0.0019 mole) of magnesium in 40 ml of methanol. The yield of 1-cyclopropyl -1-(4-trifluoromethoxyphenyl)-4-cyano-4-(4-fluoro-3-phenoxyphenyl)butane was 0.78 gram. The nmr spectrum was consistent with the proposed structure.

EXAMPLE 4

Synthesis of
1-cyclopropyl-1-(4-chlorophenyl)-4-(4-fluoro-3-phenoxyphenyl)pentane

Step A 1-(4-Fluoro-3-phenoxyphenyl)ethanol

A stirred solution of 34 ml (0.10 mole) of methylmagnesium bromide (3.0 M in diethyl ether) in 100 ml of tetrahydrofuran was cooled to 0° C., and 22.0 grams (0.10 mole) of 4-fluoro-3-phenoxybenzaldehyde was slowly added during a 30 minute period. Upon completion of addition, the reaction mixture was allowed to warm to ambient temperature at which it was stirred for two hours. At the end of this time the reaction was quenched with aqueous 10% hydrochloric acid, and the reaction mixture was extracted with two 100 ml portions of diethyl ether. The combined extracts were dried with magnesium sulfate and filtered. The filtrate was concentrated under reduced pressure, yielding 24.0 grams of 1-(4-fluoro-3-phenoxyphenyl)ethanol. The nmr spectrum was consistent with the proposed structure.

Step B Methyl (4-fluoro-3-phenoxyphenyl) ketone

This compound was prepared in a manner analogous to that of Example 1, Step D, using 5.8 grams (0.025 mole) 1-(4-fluoro-3-phenoxyphenyl)ethanol and 8.1 grams (0.038 mole) of pyridinium chlorochromate in 100 ml of methylene chloride. The yield of methyl (4-fluoro-3-phenoxyphenyl) ketone was 5.7 grams. The nmr spectrum was consistent with the proposed structure.

Step C
1-Cyclopropyl-1-(4-chlorophenyl)-2-propen-1-ol

A stirred solution of 73 ml (0.073 mole) of 1 M vinylmagnesium bromide in tetrahydrofuran was cooled in an ice water bath, and a solution of 11.0 grams (0.061 mole) of cyclopropyl 4-chlorophenyl ketone in 20 ml of tetrahydrofuran was added dropwise. Upon completion of addition, the reaction mixture was allowed to warm to ambient temperature where it was stirred for about 18 hours. After this time the reaction was quenched by the addition of 100 ml of aqueous 10% hydrochloric acid. The reaction mixture was stirred for 10 minutes and then was extracted with two 50 ml portions of diethyl ether. The combined extracts were washed with 10 ml of water and then were dried with magnesium sulfate. The mixture was filtered through a pad of silica gel, and the filtrate was concentrated under reduced pressure, yielding 11.0 grams of 1-cyclopropyl-1-(4-chlorophenyl)-2-propen-1-ol.

Step D
1-Cyclopropyl-1-(4-chlorophenyl)-3-chloro-1-propene

A stirred solution of 11.0 grams (0.053 mole) of 1-cyclopropyl-1-(4-chlorophenyl)-2-propen-1-ol and 4.6 grams (0.058 mole) of pyridine in 100 ml of diethyl ether was cooled to 0°C., and 6.8 grams (0.058 mole) of thionyl chloride was added dropwise during a 10 minute period. Upon completion of addition, the reaction mixture was stirred for 30 minutes and then was taken up in 100 ml of hexane; 50 ml of water was then carefully added. The aqueous layer was separated and was extracted with hexane. The organic layers were combined and washed with 25 ml of water and then with 25 ml of an aqueous solution saturated with sodium chloride. The organic layer was dried with magnesium sulfate and filtered. The filtrate was concentrated under reduced pressure, yielding 8.6 grams of 1-cyclopropyl-1-(4-chlorophenyl)-3-chloro-1-propene.

Step E
3-Cyclopropyl-3-(4-chlorophenyl)-2-propenyltriphenylphosphonium chloride

A stirred solution of 8.6 grams (0.038 mole) of 1-cyclopropyl -1-(4-chlorophenyl)-3-chloro-1-propene and 11.9 grams (0.045 mole) of triphenylphosphine in 20 ml of toluene was heated at reflux for six hours. After this time the reaction mixture was concentrated under reduced pressure to a residual solid. The solid was washed with 50 ml of diethyl ether yielding 3-cyclopropyl-3-(4-chlorophenyl)-2-propenyltriphenylphosphonium chloride.

Step F
1-Cyclopropyl-1-(4-chlorophenyl)-4-(4-fluoro-3-phenoxyphenyl)-1,3-pentadiene A stirred solution of 2 ml (0.005 mole) of n-butyllithium (2.5 M in hexane) in 50 ml of tetrahydrofuran was cooled to −78° C., and 2.5 grams (0.005 mole) of 3-cyclopropyl-3-(4-chlorophenyl) -2-propenyltriphenylphosphonium chloride was added quickly. Upon completion of addition, the reaction mixture was allowed to warm to 0° C. where it was stirred for one hour. After this time a solution of 1.2 grams (0.005 mole) of methyl (4-fluoro-3-phenoxyphenyl)ketone (prepared in Steps A and B of this Example) in 5 ml of tetrahydrofuran was added during a five minute period. Upon completion of addition, the reaction mixture was allowed to warm to ambient temperature where it was stirred for about 18 hours. The reaction was quenched with 50 ml of aqueous 10% hydrochloric acid, and the reaction mixture was extracted with two 50 ml portions of diethyl ether. The combined extracts were dried with magnesium sulfate and filtered. The filtrate was concentrated under reduced pressure to a residue. The residue was subjected to column chromatography on silica gel. Elution was accomplished using 10% ethyl acetate in hexane. The appropriate fractions were combined and concentrated under reduced pressure, yielding 1.2 grams of 1-cyclopropyl-1-(4-chlorophenyl)-4-(4-fluoro-3-phenoxyphenyl)-1,3-pentadiene. The nmr spectrum was consistent with the proposed structure.

Step G
1-Cyclopropyl-1-(4-chlorophenyl)-4-(4-fluoro-3-phenoxyphenyl)-2-pentene

A mixture of 0.40 gram (0.01 mole) of 1-cyclopropyl-1-(4-chlorophenyl)-4-(4-fluoro-3-phenoxyphenyl)-1,3-pentadiene and 2.43 grams (0.1 mole) of magnesium in 25 ml of methanol and 5 ml of ethanol was vigorously stirred for about 18 hours at ambient temperature. After this time the reaction was quenched with aqueous 3N hydrochloric acid, and the reaction mixture was extracted with two 25 ml portions of diethyl ether. The combined extracts were dried with magnesium sulfate and filtered. The filtrate was concentrated under reduced pressure, yielding 0.23 gram of 1-cyclopropyl-1-(4-chlorophenyl)-4-(4-fluoro-3-phenoxyphenyl)-2-pentene. The nmr spectrum was consistent with the proposed structure.

Step H
1-Cyclopropyl-1-(4-chlorophenyl)-4-(4-fluoro-3-phenoxyphenyl)pentane

Using a Parr hydrogenation apparatus, 0.23 gram (0.0005 mole) of 1-cyclopropyl-1-(4-chlorophenyl)-4-(4-fluoro-3-phenoxyphenyl)-2-pentene was hydrogenated in 50 ml of ethanol in the presence of 10% palladium on charcoal. Upon completion of the uptake of the theoretical amount of hydrogen, the reaction mixture was filtered. The filtrate was concentrated under reduced pressure, yielding 0.2 gram of 1-cyclopropyl-1-(4-chlorophenyl)-4-(4-fluoro-3-phenoxyphenyl)pentane. The nmr spectrum was consistent with the proposed structure.

EXAMPLE 5

Synthesis of 1-cyclopropyl-1-(4-chlorophenyl)-4-bromo-4-(4-fluoro-3-phenoxyphenyl)butane

Step A
(4-fluoro-3-phenoxyphenyl)methyltriphenylphosphonium chloride

A solution of 11.8 grams (0.05 mole) of 4-fluoro-3-phenoxyphenylmethyl chloride (prepared in Example 2, Step B) and 13.1 grams (0.05 mole) of triphenylphosphine in 150 mL of dry tetrahydrofuran was stirred for about 60 hours. After this time the reaction mixture was concentrated under reduced pressure to a solid residue. The solid was stirred with diethyl ether and was collected by filtration, yielding 15 grams of (4-fluoro-3-phenoxyphenyl)methyltriphenylphosphonium chloride.

Step B 3-cyclopropyl-3-(4-chlorophenyl)-2-propen-1-al

This compound was prepared in a manner analogous to that of Example 1, Step D, using 20.0 grams 1-cyclopropyl-1-(4-chlorophenyl)-2-propen-1-ol (prepared in Example 4, Step C) and 41.3 grams (0.192 mole) of pyridinium chlorochromate in 210 mL of methylene chloride. The yield of 3-cyclopropyl-3-(4-chlorophenyl)2-propen-1-al was 6.8 grams.

Step C
1-Cyclopropyl-1-(4-chlorophenyl)-4-(4-fluoro-3-phenoxyphenyl)-1,3-butadiene This compound was prepared in a manner analogous to that of Example 4, Step F, using 2.0 grams (0.01 mole) of (4-fluoro-3-phenoxyphenyl)methyltriphenylphosphonium chloride (prepared in Step A) and 3-cyclopropyl-3-(4-chlorophenyl)-2-propen-1-al and 0.7 gram (0.011 mole – 4.4 mL, 2.5 M in hexane) of n-butyllithium in 100 mL of dry tetrahydrofuran. The yield of 1-cyclopropyl-1-(4-chlorophenyl)-4-(4-fluoro-3-phenoxyphenyl)-1,3-butadiene was 1.8 grams. The nmr spectrum was consistent with the proposed structure.

Step D
1-Cyclopropyl-1-(4-chlorophenyl)-4-(4-fluoro-3-phenoxyphenyl)butane

Using a Parr hydrogenation apparatus, a solution of 1.7 grams (0.004 mole) of 1-cyclopropyl-1-(4-chlorophenyl)-4-(4-fluoro-3-phenoxyphenyl) -1,3-butadiene in 100 mL of absolute ethanol was hydrogenated in the presence of 0.3 gram of Raney nickel (50% in water). Upon completion of the hydrogenation, the reaction mixture was concentrated under reduced pressure to a residue. The residue was subjected to column chromatography on silica gel. Elution was accomplished using 10% cyclohexane in hexane. The appropriate fractions were combined and concentrated under reduced pressure, yielding 1.2 grams of 1-cyclopropyl-1-(4-chlorophenyl)-4-(4-fluoro-3-phenoxyphenyl)butane. The nmr spectrum was consistent with the proposed structure.

Step F
1-Cyclopropyl-1-(4-chlorophenyl)-4-bromo-4-(4-fluoro-3-phenoxyphenyl)butane A stirred solution of 2.0 grams (0.005 mole of 1-cyclopropyl-1-(4-chlorophenyl)-4-(4-fluoro-3-phenoxyphenyl)butane and 0.9 gram (0.005 mole) of N-bromosuccinimide in 50 mL of carbon tetrachloride was irradiated for 2 hours with a sun lamp. The reaction mixture was cooled and filtered. The filtrate was concentrated under reduced pressure, yielding 2.1 grams of 1-cyclopropyl-1-(4-chlorophenyl)-4-bromo-4-(4-fluoro-3-phenoxyphenyl)butane. The nmr spectrum was consistent with the proposed structure.

Specific examples of the compounds of this invention are set forth in Table 1and may be prepared using these and similar techniques.

In the normal use of the insecticidal and acaricidal compounds of the present invention, the compounds usually will not be employed free from admixture or dilution, but ordinarily will be used in a suitable formulated composition compatible with the method of application and comprising an insecticidally or acaricidally effective amount of the compound. The pyrethroid-like compounds of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present pyrethroid-like compounds may be applied, for example, as sprays, dusts, or granules to the area where pest control is desired, the type of application varying, of course, with the pest and the environment. Thus, the pyrethroid-like compounds of this invention may be formulated as granules of large particle size, as powdery dusts, as wettable powders, as emulsifiable concentrates, as solutions, and the like.

Granules may comprise porous or non-porous particles, such as attapulgite clay or sand, for example, which serve as carriers for the pyrethroid-like compounds. The granule particles are relatively large, a diameter of about 400–2500 microns typically. The particles are either impregnated with the pyrethroid-like compounds of this invention from solution or coated with the pyrethroid-like compound, adhesive sometimes being employed. Granules generally contain 0.05–10%, preferably 0.5–5%, active ingredient as the insecticidally effective amount.

Dusts are admixtures of the pyrethroid-like compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide or acaricide. These finely divided solids have an average particle size of less than about 50 microns. A typical dust formulation useful for controlling insects contains 1 part of the compound and 99 parts of talc.

The pyrethroid-like compounds of the present invention may be made into liquid concentrates by dissolution or emulsification in suitable liquids and into solid concentrates by admixture with talc, clays, and other known solid carriers used in the pesticide art. The concentrates are compositions containing, as a pesticidally effective amount, about 5–50% of the pyrethroid-like compound and 95–50% inert material, which includes surface-active dispersing, emulsifying, and wetting agents, but even higher concentrations of active ingredients may be employed experimentally. The concentrates are diluted with water or other liquids for practical application as sprays or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects or acarids contains 1.5 parts each of sodium lignosulfonate and sodium laurylsulfate as wetting agents, 25 parts of active ingredient, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the pyrethroid-like compound with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1-15% by weight of the insecticidal or acaricidal composition.

Other useful formulations include simple solutions of the active ingredient in a solvent in which it is completely soluble at the desired concentration, such as acetone or other organic solvents.

An insecticidally or acaricidally effective amount of pyrethroid-like compound in an insecticidal or acaricidal composition diluted for application is normally in the range of about 0.001% to about 8% by weight. Many variations of spraying and dusting compositions known in the art may be used by substituting the pyrethroid-like compounds of this invention into compositions known or apparent in the art.

The insecticidal or acaricidal compositions of this invention may be formulated with other active ingredients, including other insecticides, nematicides, acaricides, fungicides, plant growth regulators, fertilizers, etc. In using the compositions to control insects or acarids, it is only necessary that an insecticidally or acaricidally effective amount of pyrethroid-like compound be applied to the locus where control is desired. Such locus may, e.g., be the insects themselves, plants upon which the insects feed, or the insect habitat. When the locus is soil, e.g., soil in which agricultural crops are or will be planted, the active compound may be applied to and optionally incorporated into the soil. For most applications, an insecticidally or acaricidally effective amount will be about 50 to 750 g per hectare, preferably 150 g to 500 g per hectare.

A series of foliar tests were conducted to determine compound activity against the Mexican bean beetle (*Epilachna varivestis*), cabbage looper (*Trichoplusia ni*), pea aphid (*Acyrthosiphon pisum*), tobacco budworm (*Heliothis virescens*) and a phosphate susceptible strain of the twospotted spider mite (Tetranychus urticae).

Tests against the cabbage looper, Mexican bean beetle, and tobacco budworm were conducted using six to ten day old pinto bean (*Phaseolus vulgaris*) plants. These plants were sprayed to runoff on both upper and lower leaf surfaces with a 10% by volume solution of acetone in water which contained one drop of surfactant per 100 mL of solution as well as the desired amount of pesticidal compound to be tested. After treatment the plants were allowed to dry and were then removed from their pots by cutting the stems just above the soil line. The excised leaves and stems from each plant were placed in individual three ounce paper cups. Ten second instar (7-9 day old) Mexican bean beetle larvae, ten second instar (4-5 days old) cabbage looper larvae, or five second instar (4-5 days old) tobacco budworm larvae were counted into each cup. An opaque plastic lid was placed on each cup which was then held for a 48 hour exposure period at 26° C. and 50% relative humidity. At the end of the 48 hour exposure period, the cups were opened and the numbers of dead and live insects were counted. Moribund larvae which were disoriented or unable to crawl normally were counted as dead. The condition of the test plant was also observed for phytotoxicity and for reduction of feeding damage as compared to the untreated control. Two replicate tests were used for studies involving the cabbage looper and Mexican bean beetle; four replicates for those involving the tobacco budworm.

Activity of test compounds against the pea aphids was tested using fava bean plants. These plants were treated with the test compound as described above and each plant was then placed in its entirety, including the pot, into a 48 ounce waxed paper container. Ten adult pea aphids were counted into each container. A plastic domelike lid was placed on each container which was then held for a 48 hour exposure period at 26° C. and 50% humidity. Efficacy of the test chemical was determined as previously described.

Procedures to test compound activity against the twospotted spider mite were similar to those described above. Fava bean plants were treated with the test compound and each plant was placed in its entirety, including the pot, into an individual 48 ounce waxed paper container. Leaves which had been infested with adult twospotted spider mites were removed from culture plants and cut into segments containing 50-75 female mites. Each segment was placed on to the upper leaf surface of a whole pinto bean plant. After the mites had migrated to the under surfaces of the leaves, the leaf was sprayed with the test chemical solution as described above. After the plants had dried, the entire plant and the pot were placed in a metal tray in a hood. Plants were kept at 26° C. under constant light. A supply of water in the tray kept the plants turgid throughout the 48 hour exposure period.

Compound activity against the twospotted spider mite was estimated by comparing the amount of feeding damage as manifested by silvery discoloration of the leaves, and webbing on the test plants with that of the untreated control plant. Test plants which showed minimal amounts of feeding damage and webbing were examined under a microscope at approximately 10X magnification. Adult female mites on the underside of the leaf were counted, and the percent mortality was calculated from the numbers of live and dead mites observed.

The results of these tests are shown in Table 2.

Soil evaluation tests were effected using a 7.5 ppm solution which was prepared from a 16 gram/L stock solution of the active compound in acetone which was added to distilled water containing 0.1% octylphenoxy-polyethoxyethanol emulsifier, so as to obtain an active compound concentration of 15 ppm. Additional solutions of 7.5 ppm and 3.25 ppm were obtained by serial dilutions.

Four ml of the test solution was pipetted into a four ounce specimen cup containing two, two day old corn sprouts completely covered by 26 grams of dry sandy soil. The treated soil was left uncovered to allow the acetone to evaporate. Each cup was then capped and the soil in the cup was mixed thoroughly. The cap of each cup was removed and ten second instar southern corn rootworm larvae were added to each cup. The cups were each covered with lids perforated with two small holes to allow for ventilation. The cups were then exposed for 48 hours to alternating twelve hour periods of fluorescent illumination and darkness. Two replicates were run for each chemical treatment. An untreated check and appropriate standard were included in each test.

The unaffected larvae from the soil of each cup were extracted by placing the contents of each cup into a modified Berlese polyethylene funnel fitted with an 18-mesh screen. The funnels were placed over containers of an aqueous detergent solution. One hundred watt incandescent lights were placed 36 cm above the soil in each funnel. The heat from these lights slowly dried the soil causing larvae that had not been affected by the candidate insecticide to emerge from the soil and drop out of the funnel into the detergent solution. The percent mortality was determined by comparing the number of larvae in the detergent solution with the total number of larvae infested during the initiation of the test.

The results of these tests are shown in Table 3.

TABLE 1

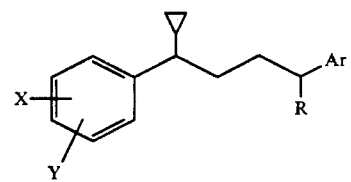

| Compound | X | Y | R | Ar |
|---|---|---|---|---|
| 1 | H | H | CN | 3-phenoxyphenyl |
| 2 | H | H | CN | 4-fluoro-3-phenoxyphenyl |
| 3 | Cl | H | CN | 3-phenoxyphenyl |
| 4 | Cl | H | CN | 4-fluoro-3-phenoxyphenyl |
| 5 | F | H | CN | 3-phenoxyphenyl |
| 6 | F | H | CN | 4-fluoro-3-phenoxyphenyl |
| 7 | —C(CH$_3$)$_3$ | H | CN | 3-phenoxyphenyl |
| 8 | —C(CH$_3$)$_3$ | H | CN | 4-fluoro-3-phenoxyphenyl |
| 9 | —OCH$_3$ | H | CN | 4-fluoro-3-phenoxyphenyl |
| 10 | OC$_2$H$_5$ | H | CN | 3-phenoxyphenyl |

TABLE 1-continued

| Compound | X | Y | R | Ar |
|---|---|---|---|---|
| 11 | —OC$_2$H$_5$ | H | CN | 4-fluoro-3-phenoxyphenyl |
| 12 | CF$_3$ | H | CN | 4-fluoro-3-phenoxyphenyl |
| 13 | OCF$_3$ | H | CN | 3-phenoxyphenyl |
| 14 | OCF$_3$ | H | CN | 4-fluoro-3-phenoxyphenyl |
| 15 | N(CH$_3$)$_2$ | H | CN | 3-phenoxyphenyl |
| 16 | Cl | H | CH$_3$ | 3-phenoxyphenyl |
| 17 | Cl | H | Br | 4-fluoro-3-phenoxyphenyl |
| 18 | H | H | CN | 2-methyl[1,1'-biphenyl]-3-yl |
| 19 | Cl | H | CN | 2-methyl[1,1'-biphenyl]-3-yl |
| 20 | OCF$_3$ | H | CN | 2-methyl[1,1'-biphenyl]-3-yl |
| 21 | H | H | CN | 6-phenoxy-2-pyridinyl |
| 22 | Cl | H | CN | 6-phenoxy-2-pyridinyl |
| 23 | OCF$_3$ | H | CN | 6-phenoxy-2-pyridinyl |
| 24 | Cl | H | —C≡CH | 3-phenoxyphenyl |
| 25 | OCF$_3$ | H | —C≡CH | 3-phenoxyphenyl |
| 26 | Cl | H | —C≡CH | 4-fluoro-3-phenoxyphenyl |
| 27 | OCF$_3$ | H | —C≡CH | 4-fluoro-3-phenoxyphenyl |
| 28 | Cl | Cl | CN | 3-phenoxyphenyl |
| 29 | —OCH$_2$—O— | | CN | 3-phenoxyphenyl |
| 30 | Cl | Cl | CN | 4-fluoro-3-phenoxyphenyl |
| 31 | —OCH$_2$—O— | | CN | 4-fluoro-3-phenoxyphenyl |
| 32 | Cl | H | CF$_3$ | 3-phenoxyphenyl |
| 33 | Cl | H | CF$_3$ | 4-fluoro-3-phenoxyphenyl |
| 34 | OCH$_2$—◁ | H | CN | 3-phenoxyphenyl |
| 35 | OCH$_2$—◁ | H | CN | 4-fluoro-3-phenoxyphenyl |
| 36 | OCH$_2$CH(CH$_3$)$_2$ | H | CN | 3-phenoxyphenyl |
| 37 | OCH$_2$CH(CH$_3$)$_2$ | H | CN | 4-fluoro-3-phenoxyphenyl |

TABLE 2

Foliar Insecticidal and Acaricidal Test Results

| | Per Cent Kill | | | | |
|---|---|---|---|---|---|
| Cmpd No. | CL | MBB | PA | TBW | TSM-S |
| 1 | 95 | 100 | 95 | 12 | 100 |
| 2 | 95 | 100 | 100 | — | 0 |
| 3 | 100 | 100 | 95 | 100 | 97 |
| 4 | 100 | 100 | 100 | 100 | 3 |

TABLE 2-continued

Foliar Insecticidal and Acaricidal Test Results

| Cmpd No. | Per Cent Kill | | | | |
|---|---|---|---|---|---|
| | CL | MBB | PA | TBW | TSM-S |
| 5 | 100 | 100 | 50 | 100 | 71 |
| 6 | 100 | 100 | 100 | 100 | 92 |
| 7 | 100 | 100 | 100 | 79 | 99 |
| 8 | 100 | 100 | 95 | 89 | 100 |
| 9 | 95 | 100 | 59 | — | 0 |
| 10 | 100 | 100 | 90 | 100 | 48 |
| 11 | 100 | 100 | 100 | 100 | 100 |
| 12 | 100 | 100 | 100 | 100 | 100 |
| 13 | 100 | 100 | 100 | 100 | 100 |
| 14 | 100 | 100 | 100 | 100 | 100 |
| *15 | 100 | 30 | 40 | — | 60 |
| 16 | 100 | 100 | 100 | 100 | 100 |
| 17 | 100 | 100 | 100 | 100 | 46 |

Application rate 1000 ppm.
CL = Cabbage looper; MBB = Mexican bean beetle, PA = Pea aphid; TBW = Tobacco budworm; TSM-S = Twospotted spider mite (phosphate susceptible).
*Test species were exposed to the treated plants for 72 hours. Exposure time for all other runs was for 48 hours.

TABLE 3

Soil Insecticidal Test Result

| Cmpd. No. | Rate (ppm) | Initial % Kill-SCR |
|---|---|---|
| 1 | 15 | 60 |
| 13 | 15 | 65 |

SCR = Southern corn rootworm.

We claim:

1. A compound of the formula

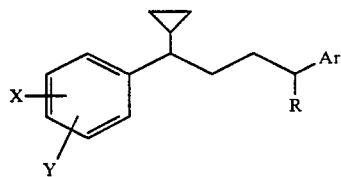

in which X and Y are independently hydrogen, halogen, alkyl($C_1$–$C_6$), alkoxy($C_1$–$C_6$), cycloalkyl($C_3$–$C_6$)alkoxy($C_1$–$C_6$), alkyl($C_1$–$C_6$)carbonyl, alkoxy($C_1$–$C_6$)carbonyl, haloalkyl($C_1$–$C_6$), haloalkoxy ($C_1$–$C_6$), alkylthio ($C_1$–$C_6$), haloalkylthio($C_1$–$C_6$), alkylsulfinyl ($C_1$–$C_6$), alkylsulfonyl ($C_1$–$C_6$), alkylamino ($C_1$–$C_6$), nitro, or cyano;

Ar is 3-phenoxyphenyl, 4-fluor-3-phenoxyphenyl, or 2-methyl(1,1'-biphenyl)-3-yl;

R is cyano;

wherein halogen and halo are fluorine, chlorine, or bromine.

2. The compound of claim 1 in which Ar is 3-phenoxyphenyl or 4-fluoro-3-phenoxyphenyl.

3. The compound of claim 2 in which X and Y are independently halogen, alkyl, alkoxy, haloalkyl, haloalkoxy, or alkylamino.

4. The compound of claim 2 in which Y is hydrogen, and X is halogen, alkyl, alkoxy, haloalkyl, haloalkoxy, or alkylamino.

5. The compound of claim 4 in which X is halogen, trifluoromethyl or trifluoromethoxy.

6. The compound of claim 5 in which X is in the 4 position.

7. The compound of claim 6 in which X is chlorine.

8. The compound of claim 7 in which Ar is 4-fluoro-3-phenoxyphenyl.

9. An insecticidal or acaricidal composition comprising an insecticidally or acaricidally effective amount of at least one compound of claim 1 in admixture with an agriculturally acceptable carrier.

10. A method for controlling insects or acarids which comprises applying to the locus where control is desired an insecticidally or acaricidally effective amount of a compound of claim 1.

11. A method for controlling insects and acarids which comprises applying to the locus where control is desired an insecticidally or acaricidally effective amount of about 50 to 750 grams per hectare of a composition of claim 9.

* * * * *